United States Patent [19]

Grohe et al.

[11] Patent Number: 4,487,783
[45] Date of Patent: Dec. 11, 1984

[54] COMBATING FUNGI WITH NOVEL (THIO-)UREAS, AND NOVEL INTERMEDIATES THEREFOR

[75] Inventors: Klaus Grohe, Odenthal; Volker Paul, Solingen, both of Fed. Rep. of Germany

[73] Assignee: Bayer Aktiengesellschaft, Leverkusen, Fed. Rep. of Germany

[21] Appl. No.: 406,695

[22] Filed: Aug. 9, 1982

[30] Foreign Application Priority Data

Aug. 19, 1981 [DE] Fed. Rep. of Germany ....... 3132690

[51] Int. Cl.$^3$ ................ C07C 127/15; C07C 157/05; A01N 9/12; A01N 9/20
[52] U.S. Cl. .................................... 424/322; 564/26; 564/28; 564/29; 564/49; 564/52; 564/54; 564/56
[58] Field of Search ............ 564/26, 29, 54, 56, 564/28, 49, 52; 424/322

[56] References Cited

U.S. PATENT DOCUMENTS

| 3,090,810 | 5/1963 | Berger et al. ............ 564/29 X |
| 3,483,296 | 12/1969 | Martin et al. ............ 564/26 X |
| 3,701,807 | 10/1972 | Chupp . |
| 3,761,241 | 9/1973 | Chupp . |
| 4,036,986 | 7/1977 | Yamada et al. ............ 424/322 |
| 4,127,673 | 11/1978 | Yamada et al. ............ 424/322 |
| 4,216,228 | 8/1980 | Yamada et al. ............ 424/322 |

FOREIGN PATENT DOCUMENTS

| 0000019 | 12/1978 | European Pat. Off. . |
| 0000376 | 1/1979 | European Pat. Off. . |
| 1518688 | 3/1969 | Fed. Rep. of Germany . |
| 2210603 | 9/1973 | Fed. Rep. of Germany . |
| 2543888 | 4/1976 | Fed. Rep. of Germany . |
| 2732257 | 1/1978 | Fed. Rep. of Germany . |
| 2439772 | 5/1980 | France . |

OTHER PUBLICATIONS

Chemical Abstracts, vol. 91, No. 1, 7/2/79, ¶ 91:1357n, and 91:1358p, p. 149.
Chemical Abstracts, vol. 94, No. 15, 4/13/81, ¶ 94:116002x and 94:116003y, p. 202.
Tetrahedron Letters, No. 29, 1973, pp. 2771–2774.

*Primary Examiner*—Thomas A. Waltz
*Attorney, Agent, or Firm*—Sprung, Horn, Kramer & Woods

[57] ABSTRACT

(Thio)-ureas of the formula

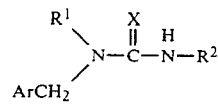

in which
  $R^1$ is an optionally alkyl-substituted cycloalkyl radical or a halogenoalkyl radical,
  $R^2$ is an alkyl or cycloalkyl radical or an optionally substituted aryl radical,
  Ar is an optionally substituted aryl radical, at least one of the radicals $R^1$, $R^2$ and Ar carrying fluorine or a fluorine-containing substituent, and
  X is an oxygen or sulphur atom, which possess fungicidal activity. Novel intermediates are also disclosed.

9 Claims, No Drawings

COMBATING FUNGI WITH NOVEL (THIO-)UREAS, AND NOVEL INTERMEDIATES THEREFOR

The present invention relates to certain new (thio-)ureas, to a process for their production and to their use as plant protection agents.

The invention also relates to certain new intermediate compounds for the production of the (thio-)ureas of the present invention.

Heavy metal salts of ethylene-bis-dithiocarbamic acid, in particular the zinc salts thereof, have been used for a relatively long time in plant protection for combating phytopathogenic fungi (see R. Wegler, Chemie der Pflanzenschutz und Schädlingsbekämpfungsmittel (Chemistry of Plant protection Agents and Pest-Combating Agents), Volume 2, 565, Springer-Verlag, Berlin, Heidelberg, New York 1970). However, their action is not always completely satisfactory when low amounts and concentrations are used.

The present invention now provides, as new compounds the (thio-)ureas of the general formula

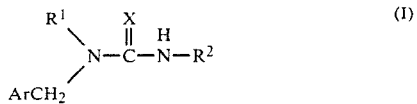

in which
$R^1$ represents an optionally alkyl-substituted cycloalkyl radical or a halogenoalkyl radical,
$R^2$ represents an alkyl or cycloalkyl radical or an optionally substituted aryl radical,
Ar represents an optionally substituted aryl radical, at least one of the radicals $R^1$, $R^2$ or Ar carrying fluorine or a fluorine-containing substituent, and
X represents an oxygen or sulphur atom.

According to the present invention we further provide a process for the production of a compound of formula (I) according to the present invention, characterized in that a secondary amine of the general formula

in which
Ar and $R^1$ have the meanings given above, is reacted with a (thio-)isocyanate of the general formula $$R^2-NCX \qquad (III),$$

in which
$R^2$ and X have the meanings given for formula (I), if appropriate in a diluent, at a temperature between $-20°$ and $150°$ C.

The amines of the formula (II) required for the preparation of the new (thio-)ureas of the formula (I) are novel and form a further subject of the present invention.

According to the present invention we further provide a process for the production of an amine of formula (II), characterized in that an aldimine of the general formula

in which
Ar and $R^1$ have the meanings given above, is reacted with a hydrogenating agent in a diluent.

The aldimines of the formula (IV) are novel and form a further subject of the present invention.

According to the present invention we further provide a process for the production of an aldimine of formula (IV), characterized in that an aldehyde of the general formula $$ArCHO \qquad (V),$$

in which
Ar has the meaning given above, is reacted with a primary amine of the general formula $$R^1-NH_2 \qquad (VI),$$

in which
$R^1$ has the meaning given above, if appropriate in a diluent, at a temperature between $0°$ and $100°$ C.

The new (thio-)ureas of the present invention of the formula (I) exhibit powerful fungicidal properties. They show a better activity compared with the prior art, in particular when low amounts and concentrations are used.

Of the new (thio-)ureas of the formula (I), those are preferred
in which
$R^1$ represents a cycloalkyl radical which has 3 to 7 carbon atoms and is optionally substituted by alkyl having 1 to 4 carbon atoms, or a halogenoalkyl having 2 to 4 carbon atoms and 1 to 5 halogen atoms (such as fluorine and chlorine atoms),
$R^2$ represents an alkyl radical having 1 to 4 carbon atoms, a cycloalkyl group having 3 to 7 carbon atoms or an optionally substituted phenyl or naphthyl radical,
Ar represents an optionally substituted phenyl radical, at least one of the radicals $R^1$, $R^2$ and Ar carrying fluorine or a fluorine-containing substituent, and
X represents an oxygen or sulphur atom.

The aryl radicals of the radicals $R^2$ and Ar independently of each other preferably carry substituents selected from halogen (such as fluorine, chlorine and bromine), $C_1$ to $C_4$ alkyl (such as methyl and ethyl), halogenoalkyl having 1 or 2 carbon atoms and 3 to 5 halogen atoms (such as fluorine and chlorine) and halogenoalkoxy and halogenothioalkoxy, each having 1 to 5 carbon atoms and up to 5 halogen atoms (such as fluorine and/or chlorine atoms).

Particularly preferred (thio-)ureas of the formula (I) are those
in which
$R^1$ represents a cycloalkyl radical having 5 or 6 carbon atoms or a halogenoalkyl radical having 2 carbon atoms and 1 to 3 fluorine atoms,
$R^2$ represents an alkyl radical having 1 or 2 carbon atoms, a cycloalkyl radical having 5 or 6 carbon atoms or an optionally substituted phenyl radical,
Ar represents an optionally substituted phenyl radical, at least one of the radicals $R^2$ and Ar carrying fluorine or a fluorine-containing substituent, and
X represents an oxygen or sulphur atom.

The phenyl radicals of the radicals $R^2$ and Ar independently of each other preferably carry substituents selected from fluorine, alkyl (such as methyl and ethyl), halogenoalkyl (such as trifluoromethyl) and halogenoalkoxy and halogenoalkylthio (such as trifluoromethoxy, 1,1,2-trifluoro-2-chloroethoxy or trifluoromethylthio).

In addition to the compounds of the formula (I) described in the preparative examples, the following compounds may be mentioned individually:

TABLE 1

Structure:
R¹\
  N–C(=X)–NH–R²
ArCH₂/

| R¹ | R² | Ar | X |
|---|---|---|---|
| cyclopentyl | 4-CF₃O-C₆H₄- | 4-F-C₆H₄- | O |
| cyclopentyl | 4-CF₃S-C₆H₄- | 4-F-C₆H₄- | O |
| cyclopentyl | 3-Cl-4-CF₃-C₆H₃- | 4-F-C₆H₄- | O |
| cyclopentyl | 2-SCF₃-C₆H₄- | 4-F-C₆H₄- | O |
| cyclopentyl | 3-Cl-4-F-C₆H₃- | 4-F-C₆H₄- | O |
| cyclopentyl | 4-HCFClCF₂O-C₆H₄- | 4-F-C₆H₄- | O |
| cyclopentyl | 4-CF₃O-C₆H₄- | 4-CF₃-C₆H₄- | O |
| cyclopentyl | 4-CF₃O-C₆H₄- | 2-CF₃-C₆H₄- | O |
| cyclopentyl | 4-CF₃O-C₆H₄- | 4-CF₃O-C₆H₄- | O |
| cyclopentyl | 4-CF₃O-C₆H₄- | 3-F-C₆H₄- | O |
| cyclopentyl | 4-CF₃O-C₆H₄- | 4-CF₃O-C₆H₄- | O |
| cyclopentyl | 4-CF₃O-C₆H₄- | 2-F-C₆H₄- | O |
| cyclopentyl | 4-CF₃S-C₆H₄- | 4-CF₃-C₆H₄- | O |
| cyclopentyl | 4-CF₃S-C₆H₄- | 2-CF₃-C₆H₄- | O |

TABLE 1-continued

| R¹ | R² | Ar | X |
|---|---|---|---|
| cyclopentyl | 4-CF₃S-C₆H₄- | 3-F-C₆H₄- | O |
| cyclopentyl | 2-SCF₃-C₆H₄- | 4-CF₃-C₆H₄- | O |
| cyclopentyl | 2-SCF₃-C₆H₄- | 2-CF₃-C₆H₄- | O |
| cyclopentyl | 3-Cl-4-F-C₆H₃- | 4-CF₃-C₆H₄- | O |
| cyclopentyl | 3-Cl-4-F-C₆H₃- | 2-CF₃-C₆H₄- | O |
| cyclopentyl | 3-Cl-4-CF₃-C₆H₃- | 4-CF₃-C₆H₄- | O |
| cyclopentyl | 3-Cl-4-CF₃-C₆H₃- | 2-F-C₆H₄- | O |
| cyclohexyl | C₆H₅ | 4-F-C₆H₄- | O |
| cyclohexyl | C₆H₅ | 4-CF₃-C₆H₄- | O |
| cyclohexyl | C₆H₅ | 4-CF₃O-C₆H₄- | O |
| cyclohexyl | 4-CF₃O-C₆H₄- | 4-Cl-C₆H₄- | O |
| cyclohexyl | 3-Cl-4-CF₃-C₆H₃- | 4-Cl-C₆H₄- | O |
| cyclohexyl | 4-CF₃S-C₆H₄- | 4-Cl-C₆H₄- | S |
| cyclohexyl | 4-F-C₆H₄- | 4-Cl-C₆H₄- | S |
| cyclopentyl | 2-naphthyl | 4-CF₃O-C₆H₄- | O |
| cyclopentyl | 1-naphthyl | 4-CF₃-C₆H₄- | O |

TABLE 1-continued $$\begin{array}{c} R^1 \quad\quad X \\ \diagdown \quad \| \quad H \\ N-C-N-R^2 \\ \diagup \\ ArCH_2 \end{array}$$

| R¹ | R² | Ar | X |
|---|---|---|---|
| CH₃-cyclopentyl | 2-CF₃-phenyl | 4-Cl-phenyl | O |
| CH₃-cyclopentyl | 4-CF₃O-phenyl | 4-Cl-phenyl | O |
| 2-CH₃-cyclohexyl | 4-F-phenyl | 4-Cl-phenyl | O |
| cyclopentyl | 4-CF₃S-phenyl | 4-Br-phenyl | O |

If, for example, N-4-fluorobenzyl-N-cyclopentylamine and phenyl isocyanate are used as starting materials, the course of the reaction according to the present invention for the production of compounds of formula (I) is illustrated by the following equation:

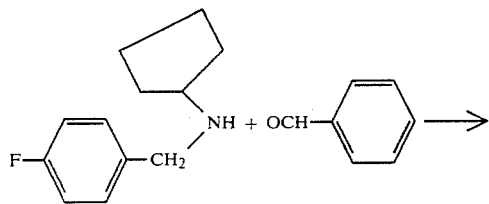

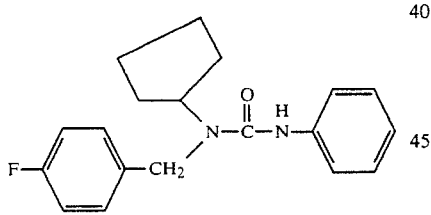

Preferred secondary amines of formula (II) and (thio-)isocyanates of formula (III) employed in carrying out the reaction according to the present invention for the production of compounds of formula (I) are those in which the radicals Ar, R² and R¹ have the meanings which have already been mentioned for these radicals in connection with the description of the preferred and particularly preferred compounds according to the present invention of the formula (I).

The secondary amines of the formula (II) employed in the process according to the invention are new. Their preparation is described in more detail later. The isocyanates of the formula (III) which are employed are generally known compounds.

The reaction, according to the invention, of the secondary amines of the formula (II), with the (thio-)isocyanates of the formula (III) can be carried out in a diluent.

In particular cases, for example when the reaction components are liquid at reaction temperature, the reaction can be carried out without a diluent. The reaction is preferably carried out in a diluent.

Inert organic solvents, for example ethers (such as dioxane), hydrocarbons (such as cyclohexane), aromatic hydrocarbons (such as benzene and toluene), chlorinated hydrocarbons (such as chloroform), and nitriles (such as acetonitrile) can be used as the diluent.

About 100 to 500 ml of diluent are employed per mol of secondary amine of the formula (II).

The reaction according to the invention is carried out at a temperature between −20° and 150° C., preferably between 0° and 100° C.

In particular cases, for example when the reaction temperature is above the boiling point of the solvent employed, the reaction can be carried out under an elevated pressure of up to about 20 bar. The reaction is preferably carried out under normal pressure.

The reaction according to the invention for the production of compounds of formula (I) can be carried out, for example, as follows:

The secondary amine in the diluent is initially introduced. The isocyanate is added to this mixture while cooling with ice. The mixture is then stirred for about ½ hour at room temperature and thereafter for about ½ hour at a slightly elevated temperature of from 30° to 60° C. After the diluent has been distilled off, the ureas according to the invention which have been obtained can be purified by crystallization.

As already mentioned, the secondary amines of the formula (II) employed in the process according to the invention are new. They are prepared by hydrogenating aldimines of the formula (IV).

If, for example, 4-fluorobenzaldehyde-cyclopentylimine and sodium borohydride are used as starting materials, the reaction according to the present invention for the production of compounds of formula (II) is illustrated by the following equation:

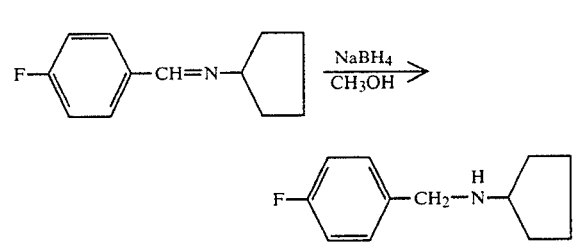

The aldimines of the formula (IV) employed in the preparation of the secondary amines of the formula (II) are new. Preferred aldimines of formula (IV) are those in which the radicals R¹ and Ar have the meanings which have been mentioned for these radicals in the description of the preferred and particularly preferred compounds of the formula (I) according to the invention. The preparation of aldimines of formula (IV) is described in more detail later.

In the preparation of the secondary amines of the formula (II), complex metal hydrides, for example lithium alanate, sodium borohydride and cobalt carbonyl hydride, are preferably used, and sodium borohydride is particularly preferably used, as the hydrogenation agent. About 1 mol of hydrogenation agent is employed per mol of aldimine of the formula (IV).

Suitable diluents are preferably alcohols, for example aliphatic alcohols (such as ethanol, n-propanol, isopropanol and n-butanol, particularly preferably methanol).

The reaction is carried out at a temperature between −20° and 60° C., preferably between −10° and 40° C.

The reaction is carried out, for example, as follows:

The hydrogenation agent and the alcohol are initially introduced. The aldimine of the formula (IV) is added dropwise to this mixture, while cooling with ice. The mixture is then stirred for approx. 1.5 hours at room temperature. About the same amount of water as the alcohol employed is then added slowly. The mixture is then extracted in the customary manner using a chlorinated hydrocarbon. The secondary amines of the formula (II) can be isolated by distillation and/or crystallization.

If, for example, 4-fluorobenzaldehyde and cyclopentylamine are used, the course of the reaction according to the present invention for the preparation of aldimines of formula (IV) is illustrated by the following equation:

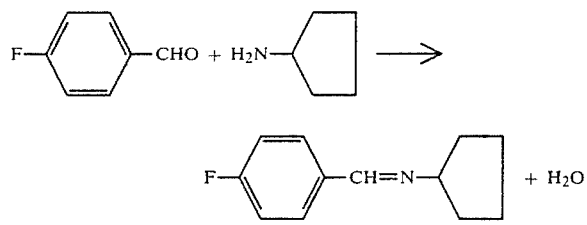

Preferred aldehydes of the formula (V) and amines of the formula (VI) employed in the preparation of the aldimines of the formula (IV) are those in which the radicals Ar and $R^1$ have the meanings which have already been mentioned for these radicals in connection with the description of the preferred and particularly preferred compounds of the formula (I) according to the invention.

The aldehydes of the formula (V) and amines of the formula (VI) which are used are generally known compounds.

The reaction of the aldehydes of the formula (V) with the amines of the formula (VI) can preferably be carried out in a diluent. Chlorinated hydrocarbons (for example chloroform and dichloromethane) are preferably employed.

The reaction is carried out at a temperature between 0° and 100° C., preferably between 20° and 50° C.

The reaction is carried out, for example, as follows:

The aldehyde of the formula (V), dissolved in a diluent, is initially introduced. The amine of the formula (VI) is added dropwise to this compound. After the exothermic reaction has ceased, the mixture is stirred for about 1 hour at room temperature. The isolation and purification of the aldimines of the formula (IV) are effected in a customary manner.

The active compounds according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration, by plants, of the active compounds, at the concentrations required for combating plant diseases, permits treatment of above-ground parts of plants, of vegetative propagation stock and seeds, and of the soil.

The good activity of the active compounds according to the invention against Pellicularia sasakii in rice should particularly be singled out. Furthermore, an interesting action against Oomycetes and scab fungi should be noted.

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in the formulations or in the various use forms as a mixture with other known active compounds, such as fungicides, bactericides, insecticides, acaricides, nematicides, herbicides, bird repellents, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They are used in the customary manner, for example by watering, immersion, spraying, atomizing, misting, vaporizing, injecting, forming a slurry, brushing on, dusting, scattering, dry dressing, moist dressing, wet dressing, slurry dressing or encrusting.

Especially in the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02%, are generally required at the place of action.

The present invention also provides fungicidal composition containing as active ingredient a compound of the present invention in admixture with a solid or liquefied gaseous diluent or carrier or in admixture with a liquid diluent or carrier containing a surface-active agent.

The present invention also provides a method of combating fungi which comprises applying to the fungi or to a habitat thereof, a compound of the present invention alone or in the form of a composition containing as active ingredient a compound of the present invention in admixture with a diluent or carrier.

The present invention further provides crops protected from damage by fungi by being grown in areas in which immediately prior to and/or during the time of the growing a compound of the present invention was applied alone or in admixture with a diluent or carrier.

It will be seen that the usual methods of providing a harvested crop may be improved by the present invention.

PREPARATIVE EXAMPLES

EXAMPLE 1

(a) Preparation of the aldimines of the formula (IV)

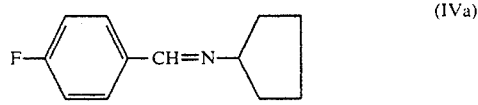

(IVa)

42.5 g of cyclopentylamine were added dropwise to 62 g (0.5 mol) of p-fluorobenzaldehyde in 150 ml of methylene chloride. After the slightly exothermic reaction had ceased, the mixture was stirred for a further hour at room temperature, the water formed was separated off, the methylene chloride was dried with $Na_2SO_4$ and filtered, and the solvent was distilled off in vacuo. Distillation of the oily residue gave 90.7 g of 4-fluoro-benzaldehydecyclopentylimide of boiling point 109° C./0.28 bar.

The following compounds were prepared according to the same method:

TABLE 2

| Compound No. | Ar—CH=N—R¹ | | Bp (°C./bar) |
|---|---|---|---|
| | Ar | R¹ | |
| IVb | CF₃—⟨⟩— | ⟨⟩— | 104/0.3 |
| IVc | ⟨⟩— (CF₃ ortho) | ⟨⟩— | 95/0.3 |
| IVd | CF₃O—⟨⟩— | ⟨⟩— | 104/0.4 |
| IVe | F—⟨⟩— (ortho) | ⟨⟩— | 80/0.1 |
| IVf | CF₃S—⟨⟩— | ⟨⟩— | 133/0.2 |
| IVg | ⟨⟩— (F ortho) | ⟨⟩— | 121/0.59 |
| IVh | ⟨⟩— | CF₃CH₂ | 43/0.12 |

Preparation of the secondary amines of the formula (II)

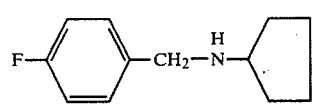

IIa 160 ml of methanol are added to 18.2 g of sodium borohydride. 90.7 g of 4-fluorobenzaldehyde-cyclopentylimide are added dropwise at 10°–15° C., while cooling with ice and stirring, and the mixture was then stirred for 1.5 hours at room temperature. 120 ml of $H_2O$ and 150 ml of methylene chloride were then added, the methylene chloride phase was separated off, and the aqueous phase was further extracted twice with $CH_2Cl_2$. The combined methylene chloride phases were washed with water and dried with $Na_2SO_4$, and the solvent was stripped off in vacuo. Distillation of the residue under a medium vacuum gave 85.9 g of N-4-fluorobenzyl-N-cyclopentylamine of boiling point 106° C. 0.25 bar.

The following compounds were prepared analogously:

TABLE 3

$$\text{Ar—CH}_2\text{—}\overset{H}{N}\text{—R}^1$$

| Compound No. | Ar | R$^1$ | Bp (°C./bar) |
|---|---|---|---|
| IIb | CF$_3$—⟨phenyl⟩— | ⟨cyclopentyl⟩ | 119/0.4 |
| IIc | ⟨phenyl with CF$_3$ ortho⟩— | ⟨cyclopentyl⟩ | 112/0.4 |
| IId | CF$_3$O—⟨phenyl⟩— | ⟨cyclopentyl⟩ | 107/0.3 |
| IIe | ⟨phenyl with F meta⟩— | ⟨cyclopentyl⟩ | 103/0.3 |
| IIf | CF$_3$S—⟨phenyl⟩— | ⟨cyclopentyl⟩ | 132/0.3 |
| IIg | ⟨phenyl with F ortho⟩— | ⟨cyclopentyl⟩ | 103/0.5 |
| IIh | ⟨phenyl⟩— | CF$_3$CH$_2$— | 83/22 |

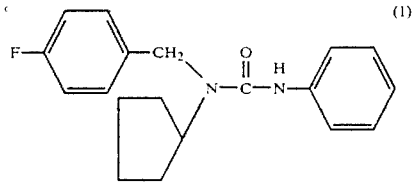

(1)

6.1 g (0.05 mol) of phenyl isocyanate were added dropwise to a solution of 9.65 g (0.05 mol) of N-4-fluorobenzyl-N-cyclopentylamine in 80 ml of anhydrous methylene chloride, while cooling with ice and stirring. The mixture was stirred for 30 minutes at room temperature and for 30 minutes at 40° C., the solvent was stripped off in vacuo, and the residue was recrystallized from acetonitrile. 14.1 g of N-4-fluorobenzyl-N-cyclopentyl-N'-phenylurea of melting point 120° to 121° C. were obtained.

EXAMPLE 2

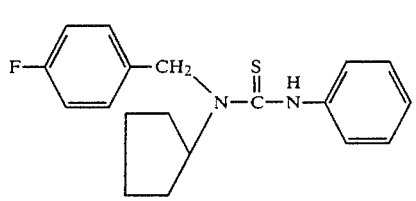

(2)

6.75 g (0.05 mol) of phenyl isothiocyanate were rapidly added dropwise to a solution of 9.65 g (0.05 mol) of N-4-fluorobenzyl-N-cyclopentylamine in 80 ml of toluene. The mixture was heated to the boil for 30 minutes, the solvent was distilled off in vacuo, and the residue was recrystallized from isopropanol. 13.8 g of N-4-fluorobenzyl-N-cyclopentyl-N'-phenylthiourea of melting point 135° C. were obtained.

The following compounds were prepared analogously:

TABLE 4

$$\text{Ar—CH}_2\diagdown\underset{R^1}{N}\text{—}\overset{X}{\underset{\|}{C}}\text{—}\overset{H}{N}\text{—R}^2$$

| Compound No. | X | R$^1$ | R$^2$ | Ar | Melting point (°C.) |
|---|---|---|---|---|---|
| 3 | O | ⟨cyclopentyl⟩ | CF$_3$O—⟨phenyl⟩— | Cl—⟨phenyl⟩— | 139 |
| 4 | O | ⟨cyclopentyl⟩ | CF$_3$S—⟨phenyl⟩— | Cl—⟨phenyl⟩— | 147 |
| 5 | O | ⟨cyclopentyl⟩ | ⟨phenyl with Cl, CF$_3$⟩— | Cl—⟨phenyl⟩— | 167 |
| 6 | O | ⟨cyclopentyl⟩ | ⟨phenyl with SCF$_3$ ortho⟩— | Cl—⟨phenyl⟩— | 90 |
| 7 | O | ⟨cyclopentyl⟩ | ⟨phenyl with Cl, F⟩— | Cl—⟨phenyl⟩— | 132 |

TABLE 4-continued

Ar—CH$_2$—N(R$^1$)—C(=X)—N(H)—R$^2$

| Compound No. | X | R$^1$ | R$^2$ | Ar | Melting point (°C.) |
|---|---|---|---|---|---|
| 8 | O | cyclopentyl | HCFClCF$_2$O—C$_6$H$_4$— | 4-Cl-C$_6$H$_4$— | 128 |
| 9 | O | cyclopentyl | C$_6$H$_5$ | 4-CF$_3$-C$_6$H$_4$— | 133 |
| 10 | O | cyclopentyl | C$_6$H$_5$ | 2-CF$_3$-C$_6$H$_4$— | 191 |
| 11 | O | cyclopentyl | C$_6$H$_5$ | 4-CF$_3$O-C$_6$H$_4$— | 108 |
| 12 | O | cyclopentyl | C$_6$H$_5$ | 3-F-C$_6$H$_4$— | 130 |
| 13 | O | cyclopentyl | C$_6$H$_5$ | 4-CF$_3$S-C$_6$H$_4$— | 149 |
| 14 | O | cyclopentyl | C$_6$H$_5$ | 2-F-C$_6$H$_4$— | 153 |
| 15 | O | cyclopentyl | 4-CH$_3$-C$_6$H$_4$— | 2-F-C$_6$H$_4$— | 149 |
| 16 | O | cyclopentyl | 4-CH$_3$-C$_6$H$_4$— | 4-F-C$_6$H$_4$— | 116 |
| 17 | O | cyclopentyl | 4-CH$_3$-C$_6$H$_4$— | 4-CF$_3$-C$_6$H$_4$— | 141 |
| 18 | O | cyclopentyl | 4-CH$_3$-C$_6$H$_4$— | 2-CF$_3$-C$_6$H$_4$— | 198 |
| 19 | O | cyclopentyl | 4-CH$_3$-C$_6$H$_4$— | 4-CF$_3$S-C$_6$H$_4$— | 149 |
| 20 | O | cyclopentyl | 4-CH$_3$-C$_6$H$_4$O— | 3-F-C$_6$H$_4$— | 145 |
| 21 | O | cyclopentyl | 4-CH$_3$-C$_6$H$_4$— | 4-CF$_3$O-C$_6$H$_4$— | 125 |
| 22 | O | cyclopentyl | CH$_3$ | 2-F-C$_6$H$_4$— | 145 |
| 23 | O | cyclopentyl | cyclohexyl | 2-F-C$_6$H$_4$— | 109 |

TABLE 4-continued $$Ar-CH_2 \diagdown N-\underset{\underset{R^1}{|}}{\overset{\overset{X}{\|}}{C}}-\underset{H}{N}-R^2$$

| Compound No. | X | R$^1$ | R$^2$ | Ar | Melting point (°C.) |
|---|---|---|---|---|---|
| 24 | O | cyclopropyl | 3,4-Cl$_2$C$_6$H$_3$ | 2-F-C$_6$H$_4$ | 144 |
| 25 | O | CF$_3$CH$_2$— | C$_6$H$_5$ | C$_6$H$_5$ | 124 |
| 26 | S | CF$_3$CH$_2$ | C$_6$H$_5$ | C$_6$H$_5$ | 96 |
| 27 | O | CF$_3$CH$_2$ | 4-CH$_3$-C$_6$H$_4$ | C$_6$H$_5$ | 120 |
| 28 | O | CF$_3$CH$_2$ | CH$_3$ | C$_6$H$_5$ | 56 |
| 29 | O | CF$_3$CH$_2$ | cyclohexyl | C$_6$H$_5$ | 94 |
| 30 | S | cyclopropyl | C$_6$H$_5$ | 2-F-C$_6$H$_4$ | 81 |
| 31 | S | cyclopropyl | C$_6$H$_5$ | 4-CF$_3$-C$_6$H$_4$ | 129 |
| 32 | S | cyclopropyl | C$_6$H$_5$ | 2-CF$_3$-C$_6$H$_4$ | 138 |
| 33 | S | cyclopropyl | C$_6$H$_5$ | 3-F-C$_6$H$_4$ | 110 |
| 34 | S | cyclopropyl | C$_6$H$_5$ | 4-CF$_3$-C$_6$H$_4$ | 119 |
| 35 | S | cyclopropyl | C$_6$H$_5$ | 4-CF$_3$O-C$_6$H$_4$ | 127 |

The fungicidal activity of the compounds of this invention is illustrated by the following biotest example.

In this example, the compounds according to the present invention are each identified by the number (given in brackets) from Examples 1 and 2 and Table 4.

EXAMPLE 3

Pellicularia test (rice)
Solvent: 12.5 parts by weight of acetone
Emulsifier: 0.3 part by weight of alkylaryl polyglycol ether To produce a suitable preparation of active compound, 1 part by weight of active compound was mixed with the stated amount of solvent, and the concentrate was diluted with water and the stated amount of emulsifier, to the desired concentration.

To test for activity, young rice plants in the 3 to 4 leaf stage were sprayed until dripping wet. The plants remained in a greenhouse until they had dried off. The plants were then inoculated with Pellicularia sasakii and were placed at 25° C. and 100% relative atmospheric humidity.

The evaluation of the disease infestation was carried out 5 to 8 days after the inoculation.

In this test, a clearly superior activity compared with the prior art was shown, for example, by the compounds (1), (9) and (13).

It will be appreciated that the instant specification and examples are set forth by way of illustration and not limitation, and that various modifications and changes may be made without departing from the spirit and scope of the present invention.

What is claimed is:
1. A urea of the formula

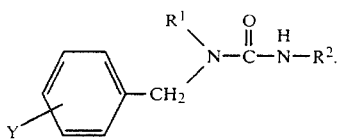

in which

Y is fluorine, trifluoromethyl, trifluoromethoxy, trifluoromethylthio, or 1,1,2-trifluoro-2-chlorethoxy $R^1$ is a cycloalkyl radical which has 3 to 7 carbon atoms and is optionally substituted by alkyl having 1 to 4 carbon atoms, or a halogenoalkyl radical having 2 to 4 carbon atoms and 1 to 5 halogen atoms, and $R^2$ is an alkyl radical having 1 to 4 carbon atoms, a cycloalkyl radical having 3 to 7 carbon atoms or a phenyl or naphthyl radical optionally substututed by halogen, $C_1$ to $C_4$ alkyl, halogenoalkyl having 1 or 2 carbon atoms and 3 to 5 halogen atoms, or halogenoalkoxy or halogenothioalkoxy each having 1 to 5 carbon atoms and up to 5 halogen atoms.

2. A compound according to claim 1, in which $R^1$ is a cycloalkyl radical having 5 or 6 carbon atoms or a halogenoalkyl radical having 2 carbon atoms and 1 to 3 fluorine atoms, and $R^2$ is an alkyl radical having 1 or 2 carbon atoms, a cycloalkyl radical having 5 or 6 carbon atoms or a phenyl radical optionally substituted as indicated.

3. A compound according to claim 1, wherein such compound is N-4-fluorobenzyl-N-cyclopentyl-N'-phenylurea of the formula

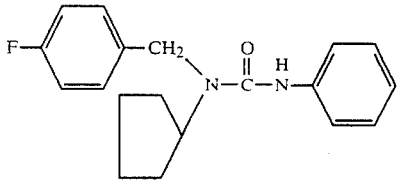

4. A compound according to claim 1, wherein such compound is N-4-trifluoromethylbenzyl-N-cyclopentyl-N'-phenylurea of the formula

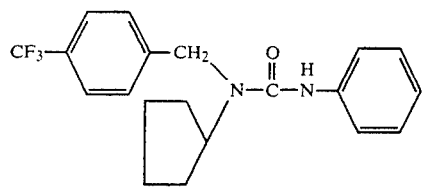

5. A compound according to claim 1, wherein such compound is N-4-trifluoromethyoxybenzyl-N-cyclopentyl-N'-phenylurea of the formula

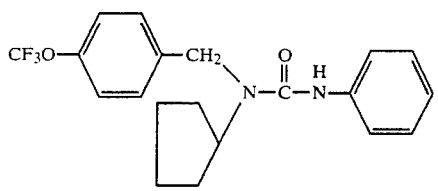

6. A compound according to claim 1, wherein such compound is N-4-trifluoromethylmercaptobenzyl-N-cyclopentyl-N'-p-tolylurea of the formula

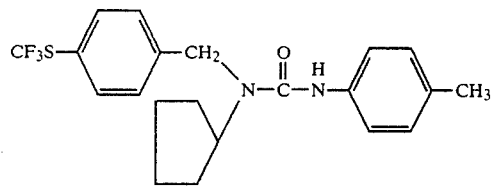

7. A fungicidal composition comprising as active ingredient a fungicidally effective amount of a compound according to claim 1 in admixture with a diluent.

8. A method of combating fungi comprising applying to the fungi, or to a habitat thereof, a fungicidally effective amount of a compound according to claim 1.

9. The method according to claim 8, wherein such compound is

N-4-fluorobenzyl-N-cyclopentyl-N'-phenylurea,
N-4-trifluoromethylbenzyl-N-cyclopentyl-N'-phenylurea,
N-4-trifluoromethoxybenzyl-N-cyclopentyl-N'-phenylurea, or
N-4-trifluoromethylmercaptobenzyl-N-cyclopentyl-N'-p-tolylurea.

* * * * *